United States Patent
Burchfield

(10) Patent No.: US 9,564,290 B2
(45) Date of Patent: Feb. 7, 2017

(54) MICRO MACHINED TWO DIMENSIONAL FARADAY COLLECTOR GRID

(71) Applicant: Hamilton Sundstrand Corporation, Charlotte, NC (US)

(72) Inventor: David E. Burchfield, Rancho Cucamonga, CA (US)

(73) Assignee: Hamilton Sundstrand Corporation, Charlotte, NC (US)

( * ) Notice: Subject to any disclaimer, the term of this patent is extended or adjusted under 35 U.S.C. 154(b) by 115 days.

(21) Appl. No.: 14/543,924

(22) Filed: Nov. 18, 2014

(65) Prior Publication Data
US 2016/0141145 A1    May 19, 2016

(51) Int. Cl.
| | |
|---|---|
| H01J 37/00 | (2006.01) |
| H01J 37/244 | (2006.01) |
| H01J 49/02 | (2006.01) |
| G01N 27/62 | (2006.01) |
| H01J 49/00 | (2006.01) |

(52) U.S. Cl.
CPC ........... *H01J 37/244* (2013.01); *G01N 27/622* (2013.01); *H01J 49/0095* (2013.01); *H01J 49/025* (2013.01); *H01J 2237/24405* (2013.01)

(58) Field of Classification Search
USPC ........................................................ 250/283
See application file for complete search history.

(56) References Cited

U.S. PATENT DOCUMENTS

| | | | |
|---|---|---|---|
| 4,066,894 A | 1/1978 | Hunt et al. | |
| 4,124,801 A | 11/1978 | Cook et al. | |
| 4,524,275 A | 6/1985 | Cottrell et al. | |
| 4,608,493 A | 8/1986 | Hayafuji | |
| 5,814,823 A | 9/1998 | Benveniste | |
| 5,986,258 A * | 11/1999 | Park | H01J 49/40 250/287 |
| 6,452,165 B1 | 9/2002 | Schwieters | |
| 7,579,589 B2 * | 8/2009 | Miller | G01N 30/7206 250/281 |
| 8,866,080 B2 * | 10/2014 | Bower | H01J 37/244 250/336.1 |
| 2006/0231751 A1 | 10/2006 | Zuleta et al. | |

FOREIGN PATENT DOCUMENTS

| | | |
|---|---|---|
| EP | 0559202 A1 | 9/1993 |
| WO | 03065763 A1 | 8/2003 |

OTHER PUBLICATIONS

European Search Report for European Application No. 15194047.5 mailed Apr. 5, 2016.

* cited by examiner

*Primary Examiner* — Phillip A Johnston
(74) *Attorney, Agent, or Firm* — Carlson, Gaskey & Olds, PC

(57) ABSTRACT

A system for detecting particles in a gas stream comprises a Faraday collector separating charged particles into positive and negative streams to be detected. The Faraday collector includes a plurality of interdigitated wires, with a first plurality of wires charged with a positive potential and a second plurality of wires charged with a negative potential to separate particles in the gas stream into the positive and negative streams.

20 Claims, 1 Drawing Sheet

MICRO MACHINED TWO DIMENSIONAL FARADAY COLLECTOR GRID

BACKGROUND OF THE INVENTION

This application relates to a grid utilized in a detector for instruments such as ion mobility and differential mobility spectrometers.

Ion mobility spectrometers (IMS) are utilized to identify trace materials in a gas stream. As an example, IMS instruments are known which detect the presence of trace amounts of chemical warfare agents, toxic industrial chemicals, or improvised explosive devices.

One type of IMS is known as a time of flight spectrometer. In time of flight, air is first ionized and then a gating device allows a small fraction of the ions to be analyzed to move into a drift tube. An electric field is applied along the drift tube and chemical species are separated based on their relative mobility, which in turn is a function of the ion's molecular weight and size Downstream of the drift tube, there is typically a collector to communicate the collected ionized particles to a detector.

In some instances, the ionized particles can have both positive and negative ions. It would be efficient to detect both species simultaneously. However, proposals to date have required large electric fields and, thus, have complicated other locations along the detector system.

It has been known to make micro machined fine electrode grids. However, this type grid has been utilized for gating devices in such sensing systems and not at the collector location.

SUMMARY OF THE INVENTION

A system for detecting particles in a gas stream comprises a Faraday collector separating charged particles into positive and negative streams to be detected. The Faraday collector includes a plurality of interdigitated wires, with a first plurality of wires charged with a positive potential and a second plurality of wires charged with a negative potential to separate particles in the gas stream into the positive and negative streams.

These and other features may be best understood from the following drawings and specification.

DETAILED DESCRIPTION

Figure 1:
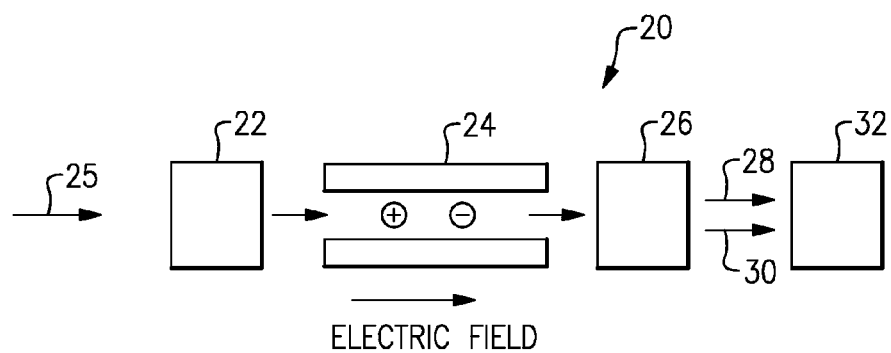
FIG. 1 shows a differential mobility sensing system.

As shown in FIG. 1, an ion mobility system 20 is a device for detecting molecules and particulates in air. These systems have a mechanism 22 for imparting charge on the air constituents, usually a corona discharge source or a radioactive ionization source; a mechanism 24 for separating the ions by size, such as a drift tube or differential mobility cell; and a mechanism 26 for detecting the ions, such as one or more Faraday collectors. Where the ions are separated by size using time of flight spectrometry, the analyzer has a gating device for gating a portion of a gas stream into the drift tube 24. The drift tube 24 applies an electric field to the ionized particles, drawing the ions down the tube at velocities dependent on the field strength and the ion diameters. At the end of the drift tube the ions are delivered to Faraday collector 26. In time of flight ion mobility only ions of positive or negative charge are delivered to the collector at any one time, based on the polarity electric field drawing ions through the drift region.

In differential mobility spectrometers, however, ions of both polarities are driven through the analyzer under a flow of air and separation is effected by a high frequency asymmetric radio-frequency field. Where positive and negative ions co-exist, the Faraday collector first separate the particles into a positive and negative streams. The disclosed Faraday collector 26 is for this application, and includes a plurality of interdigitated wires. A first plurality of the wires are charged with a positive potential and a second plurality of the wires are charged with a negative potential to separate particles in the gas stream into the positive and negative streams. The separated ion streams are collected on the alternating positively and negatively charged wires for detection.

The sensing system 20 may be a differential mobility sensor, also known as a field asymmetric ion mobility spectrometry system. Alternatively, other types of sensing systems which utilize a Faraday collector may benefit from this disclosure.

As shown in FIG. 1, different particles may receive both positive and negative ions. The ionized particles pass to Faraday collector 26 and the disclosed Faraday collector separates the particles into a positive ion stream 28 and a negative ion stream 30. The ion streams 28 and 30 pass to a detector 32. The system, as disclosed to this point, other than the collector 26, may function as known.

Figures 2, 3:
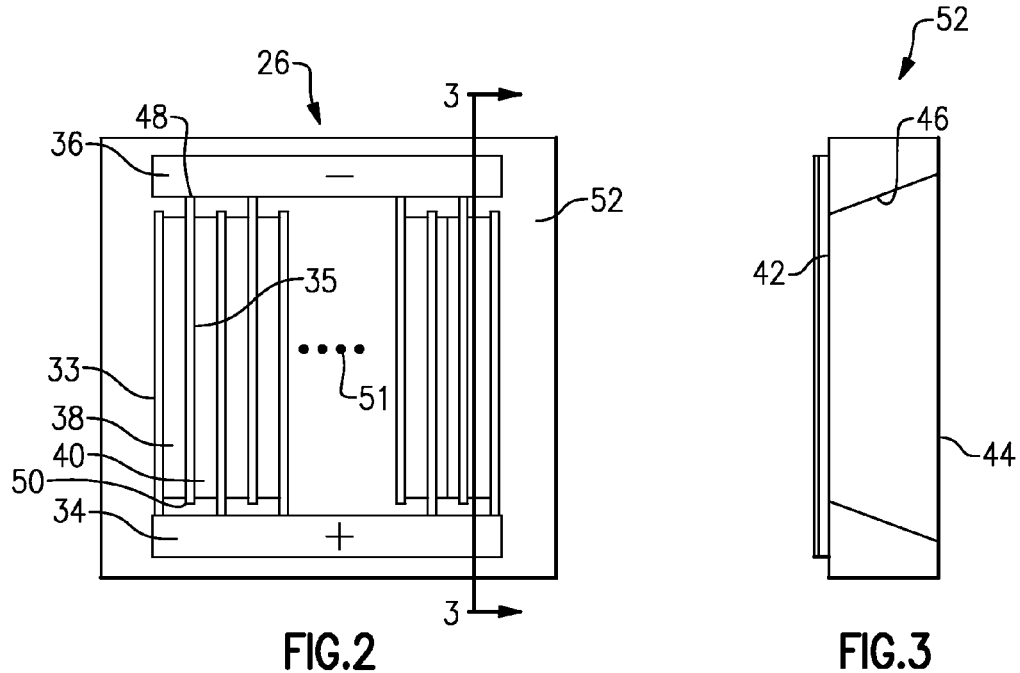
FIG. 2 shows a collector.
FIG. 3 is a cross-section along line 3-3 of FIG. 2.

FIG. 2 shows an embodiment of a Faraday collector 26. A grid is provided by a plurality of wires 33 associated with a first bus 34 and carrying a positive charge and a second plurality of fine wires 35 extending from a second bus 36 and carrying a negative charge. A plurality of channels 38 and 40 between the wires 33 and 35 will receive the charged particles downstream of the drift tube 24 of FIG. 1. The wires will attract or repel the ions based upon the ion charge and, thus, facilitate the separation into the streams 28 and 30, as shown in FIG. 1. The numeral 51 schematically shows there may be many more channels.

The collector 26 generally could be described as a grid of fine wires placed close together and biased alternatively with relatively small potentials. In one example, a grid of 50 micron thick wires may be spaced 200 microns to define the channels 38 and 40. Wires could span one centimeter between ends 48 and 50. In embodiments, the wires may be less than 100 microns thick and spaced by less than 400 microns.

Potentials of plus or minus 20 volts or less may be utilized. In other embodiments, potentials of 10 or less volts may be utilized. In one specific embodiment, plus or minus five volts were applied to the buses 36 and 38.

In an example, where potentials of plus and minus 10 volts are utilized, a field of 1,000 volts/centimeters is provided between the wires, driving ions of both types to the appropriate wires. However, the field will cancel out approximately one grid spacing in front of and behind the collector 26. Thus, operation of collector 26 does not impact upon upstream or downstream components of the overall system.

The collector 26 may be micro machined from a silicon material. Silicon based materials will provide a relatively stiff set of wires and limit the sensitivity of the detector to microphonics. It also simplifies manufacture.

In one embodiment, the aperture 42 was 0.5 centimeter. The wires were 10 micron thick and 50 microns wide. The wires had 10 ohms/cm² silicon contacting along an entire length with one micron of platinum. A substrate 52 surrounding the electric components may be 10 ohms/cm² silicon and be 500 microns thick. The substrate is maintained at a local ground.

The substrate 52 may have a shape as shown in FIG. 3, with an entrance aperture 42. An exit 44 can be seen as bring larger. Sidewalls 46 may be ramped outwardly.

On the other hand, other approaches to providing interdigitated electrodes at moderate to high pitch could include chemical etching or photolithography.

Although an embodiment of this invention has been disclosed, a worker of ordinary skill in this art would recognize that certain modifications would come within the scope of this invention. For that reason, the following claims should be studied to determine the true scope and content of this invention.

The invention claimed is:

1. A system for detecting particles in a gas stream comprising:
   a Faraday collector separating charged particles into positive and negative streams to be detected;
   said Faraday collector including a plurality of interdigitated wires, with a first plurality of said wires charged with a positive potential and a second plurality of said wires charged with a negative potential to separate particles in the gas stream into the positive and negative streams;
   the potential on said fine wires being less than 20 volts; and
   alternating ones of said wires being charged with the positive and negative potentials.

2. The system as set forth in claim 1, wherein the potential is less than 10 volts.

3. The system as set forth in claim 1, wherein a thickness of said wires is less than 100 micron, and a spacing between adjacent ones of said wires is less than 400 micron.

4. The system as set forth in claim 1, wherein a positive bus is formed at one side of said collector and a negative bus is formed at a second side of said collector and one of said buses communicate with each of said first and second plurality of wires.

5. The system as set forth in claim 4, wherein channels are formed between adjacent ones of said wires to receive the gas flow.

6. The system as set forth in claim 5, wherein said Faraday collector is formed of a silicon material.

7. The system as set forth in claim 4, wherein said bus and said wires are received in a substrate and said substrate is grounded.

8. The system as set forth in claim 1, wherein an electric field from said Faraday collector is canceled out at less than twice a spacing between adjacent ones of said plurality of wires both upstream and downstream of said Faraday collector.

9. The system as set forth in claim 8, wherein a thickness of said wires is less than 100 micron, and a spacing between adjacent ones of said wires is less than 400 micron.

10. The system as set forth in claim 1, wherein a positive bus is formed at one side of said collector and a negative bus is formed at a second side of said collector and one of said buses communicate with each of said first and second plurality of wires.

11. The system as set forth in claim 1, wherein channels are formed between adjacent ones of said wires to receive the gas flow.

12. The system as set forth in claim 1, wherein said bus and said wires are received in a substrate and said substrate is grounded.

13. An ion mobility system comprising:
    a first mechanism for imparting charge on air constituents,
    a second mechanism for separating ions by size, and a Faraday collector for separating charged particles into positive and negative streams to be detected; and
    said Faraday collector including a plurality of interdigitated wires, with a first plurality of said wires charged with a positive potential and a second plurality of said wires charged with a negative potential to separate particles in the gas stream into the positive and negative streams;
    the potential on said fine wires being less than 20 volts; and
    alternating ones of said wires being charged with the positive and negative potentials.

14. The system as set forth in claim 13, wherein said first mechanism is one of a corona discharge source and a radial active ionization source.

15. The system as set forth in claim 13, wherein said second mechanism is one of a drift tube or a differential mobility cell.

16. The system as set forth in claim 13, wherein a thickness of said wires is less than 100 micron, and a spacing between adjacent ones of said wires is less than 400 micron.

17. The system as set forth in claim 13, wherein a positive bus is formed at one side of said collector and a negative bus is formed at a second side of said collector and one of said buses communicate with each of said first and second plurality of wires.

18. The system as set forth in claim 13, wherein channels are formed between adjacent ones of said wires to receive the gas flow.

19. The system as set forth in claim 13, wherein said bus and said wires are received in a substrate and said substrate is grounded.

20. The system as set forth in claim 13, wherein an electric field from said Faraday collector is canceled out at less than twice a spacing between adjacent ones of said plurality of wires both upstream and downstream of said Faraday collector.

* * * * *